(12) United States Patent
Oh et al.

(10) Patent No.: US 8,343,555 B2
(45) Date of Patent: Jan. 1, 2013

(54) COMPOSITION AND METHOD FOR TREATING OR PREVENTING WHITE SPOT SYNDROME VIRUS

(75) Inventors: Hwa-Gyun Oh, Gyeonggi-do (KR);
Ki-Hong Sung, Seoul (KR);
Hong-Ryeol Jeon, Gyeonggi-do (KR);
Hong-Suk Kye, Gyeonggi-do (KR);
Se-Geun Yu, Gyeonggi-do (KR);
Dong-Jin Ha, Gyeonggi-do (KR)

(73) Assignee: CTC Bio, Inc., Seoul (KR)

( * ) Notice: Subject to any disclaimer, the term of this patent is extended or adjusted under 35 U.S.C. 154(b) by 841 days.

(21) Appl. No.: 12/303,007

(22) PCT Filed: May 29, 2007

(86) PCT No.: PCT/KR2007/002602
§ 371 (c)(1),
(2), (4) Date: Dec. 1, 2008

(87) PCT Pub. No.: WO2007/139337
PCT Pub. Date: Dec. 6, 2007

(65) Prior Publication Data
US 2009/0258077 A1    Oct. 15, 2009

(30) Foreign Application Priority Data

May 30, 2006 (KR) .................. 10-2006-0048780

(51) Int. Cl.
*A61K 36/282* (2006.01)
*A61K 36/00* (2006.01)
(52) U.S. Cl. .......................... 424/740; 424/725
(58) Field of Classification Search .................. None
See application file for complete search history.

(56) References Cited

U.S. PATENT DOCUMENTS

| 2004/0137202 A1* | 7/2004 | Hamilton et al. ............ 428/174 |
| 2005/0059647 A1 | 3/2005 | Sas et al. |

FOREIGN PATENT DOCUMENTS

| EP | 0568001 | 11/1993 |
| JP | 55-094392 | 7/1980 |
| JP | 04-128237 | 4/1992 |
| KR | 10-2006-0042298 | 5/2006 |

OTHER PUBLICATIONS

DW ACC 2004-416464, Feb. 2004, Derwent or KR20, Lee.*
DW ACC 2002-729338, Apr. 2002, Derwent or KR20, Hwang et al.*
DW ACC 1999-539174, Sep. 1999, Derwent, Eaton et al.*
Herbs: *Artemisia japonica* Oriental' (www.digthedirt.com/plants/35221-herbs-artemisia-japonica-oriental/sources, pp. 2-4).*
Marielle C. W. van Hulten et al., "Analysis of a genomic segment of white spot syndrome virus of shrimp containing ribonucleotide reductase genes and repeat regions," *Journal of General Virology*, 2000, 81:307-316.
J.M. Vlak et al., "Nimaviridae, A new virus family infecting aquatic invertebrates," XII International Congress of Virology, Paris, 2002.
Newman, S.G., "A Review of the Use of Non Specific Immune-Stimulants to Reduce the Impact of the WSSV," Fifth Ecuadorian Aquaculture Conference, Oct. 28-30, 1999.
Direkbusarakom S., et al., "Protective Efficacy of *Clinacanthus nutans* on Yellow-head Disease in Black Tiger Shrimp (*Penaeus monodan*)," *Fish Pathology*, 1998, 33(4):401-404.
Direkbusarakom S., et al., "Antiviral Activity of Several Thai Traditional Herb Extracts against Fish Pathogenic Viruses," *Fish Pathology*, 1996, 31(4):209-213.
Direkbusarakom S., et al., "Effect of *Phyllanthus* spp. against yellow-head baculovirus infection in black tiger shrimp, *Penaeus monodon*," *Diseases in Asian Aquaculture II*, Fish Health Section, Asian Fisheries Society Manila, 1995, 81-88.
Kwon, H.C. et al., "Phytochemical Constituents of *Artemisia japonica* ssp. *littoricola*," *Arch. Pharm. Res.*, 2001, 24(3):194-197.
Chung, Y.G. et al., "The Efficacy of *Saururus chinensis* on Cervical Cancer Cells: The Inhibitory Effect on the Function of E6 and E7 Oncogenes of HPV Type 16," *J. Pharm. Soc. Korea*, 2002, 46(6):426-432.

* cited by examiner

*Primary Examiner* — Christopher R Tate
*Assistant Examiner* — Randall Winston
(74) *Attorney, Agent, or Firm* — Jones Day

(57) ABSTRACT

The present invention relates to a composition and method for treating or preventing white spot syndrome virus of arthropod. The present invention is based on using *Artemisia japonica* extract, and preferably, a mixture of *Artemisia japonica* extract and *Saururus chinensis* extract as effective agent. More preferably, the present invention provides a composition for treating or preventing white spot syndrome virus, comprising *Artemisia japonica* extract and *Saururus chinensis* extract which are coated by a polymer. The present invention also provides a method for treating or preventing white spot syndrome virus of arthropod, using *Artemisia japonica* extract and *Saururus chinensis* extract which are coated by a polymer.

7 Claims, 6 Drawing Sheets

[Fig. 1]
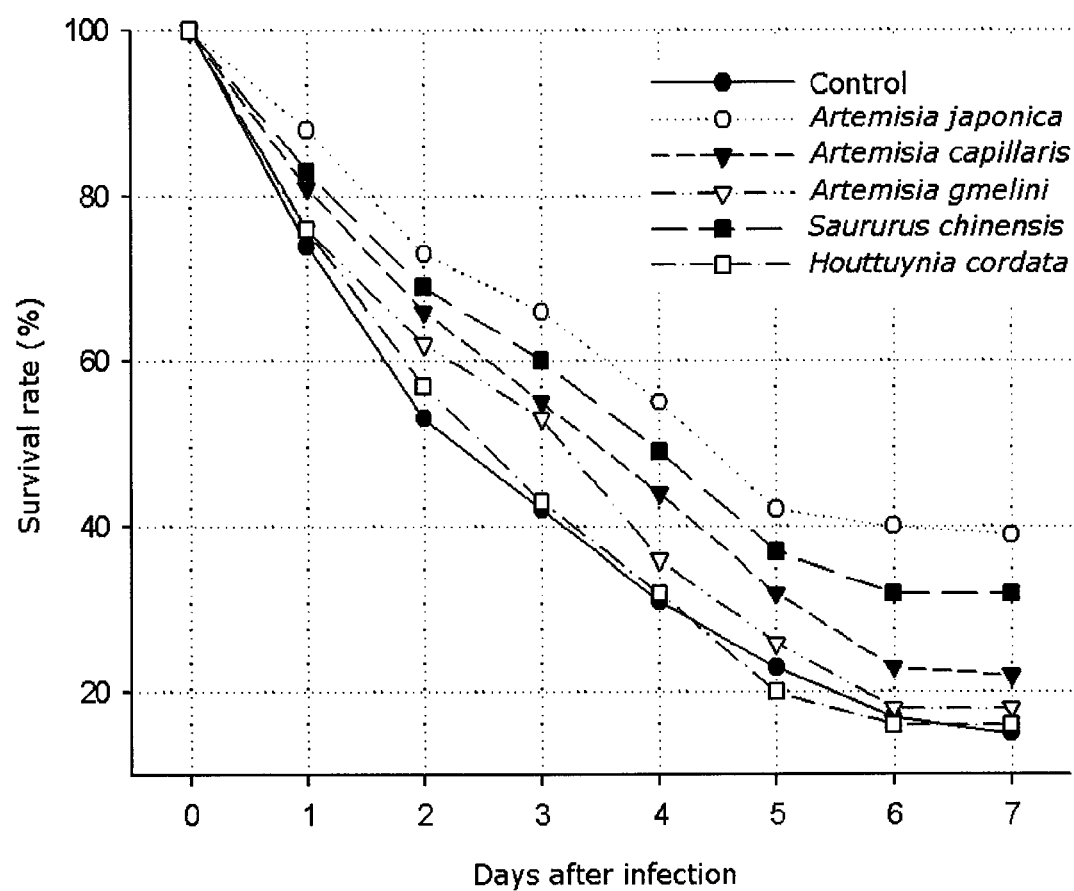

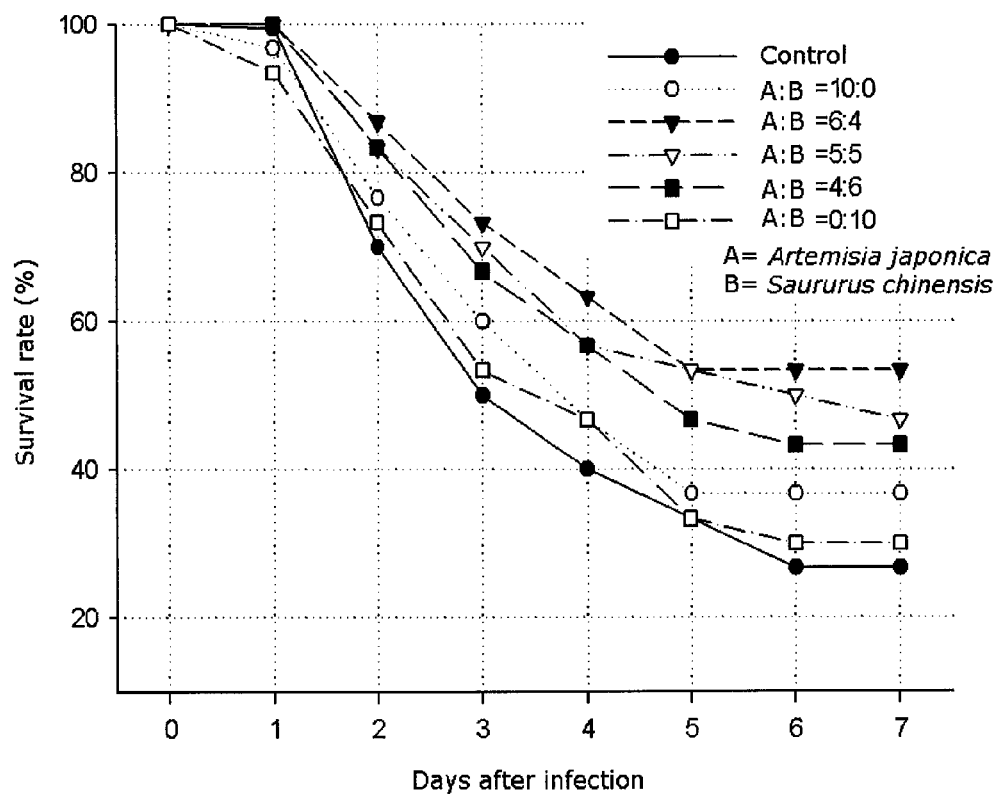
[Fig. 2]

[Fig. 3]
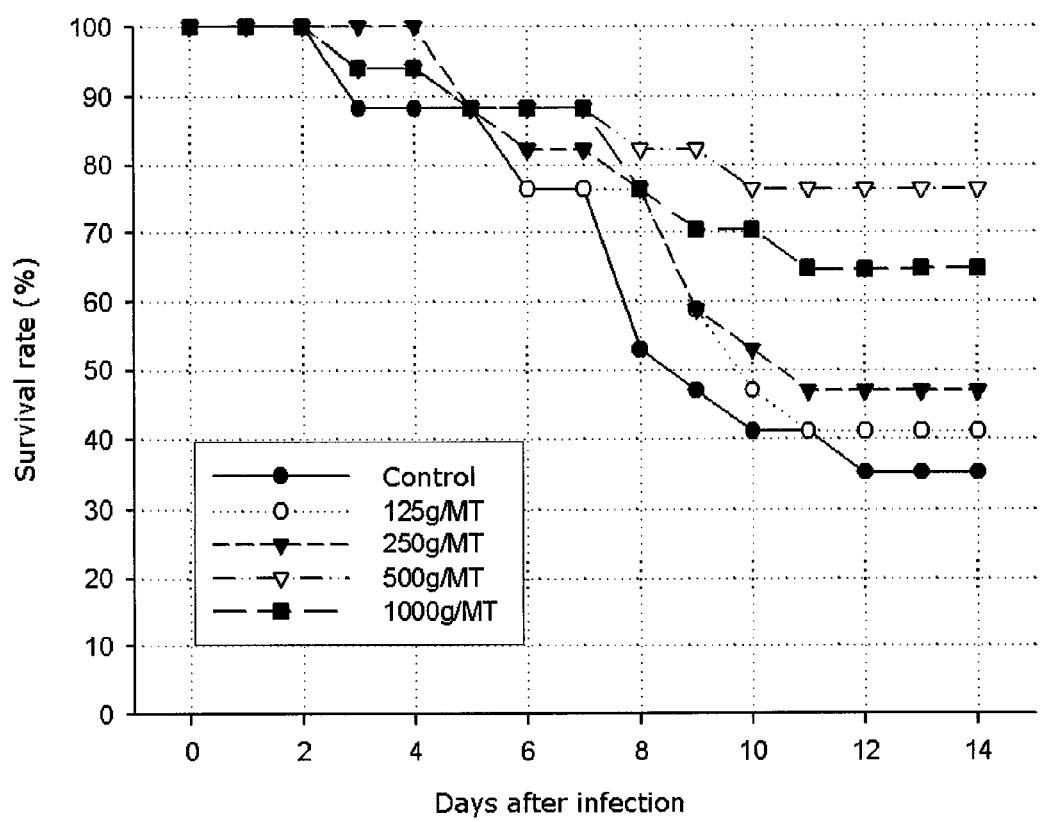

[Fig. 4]
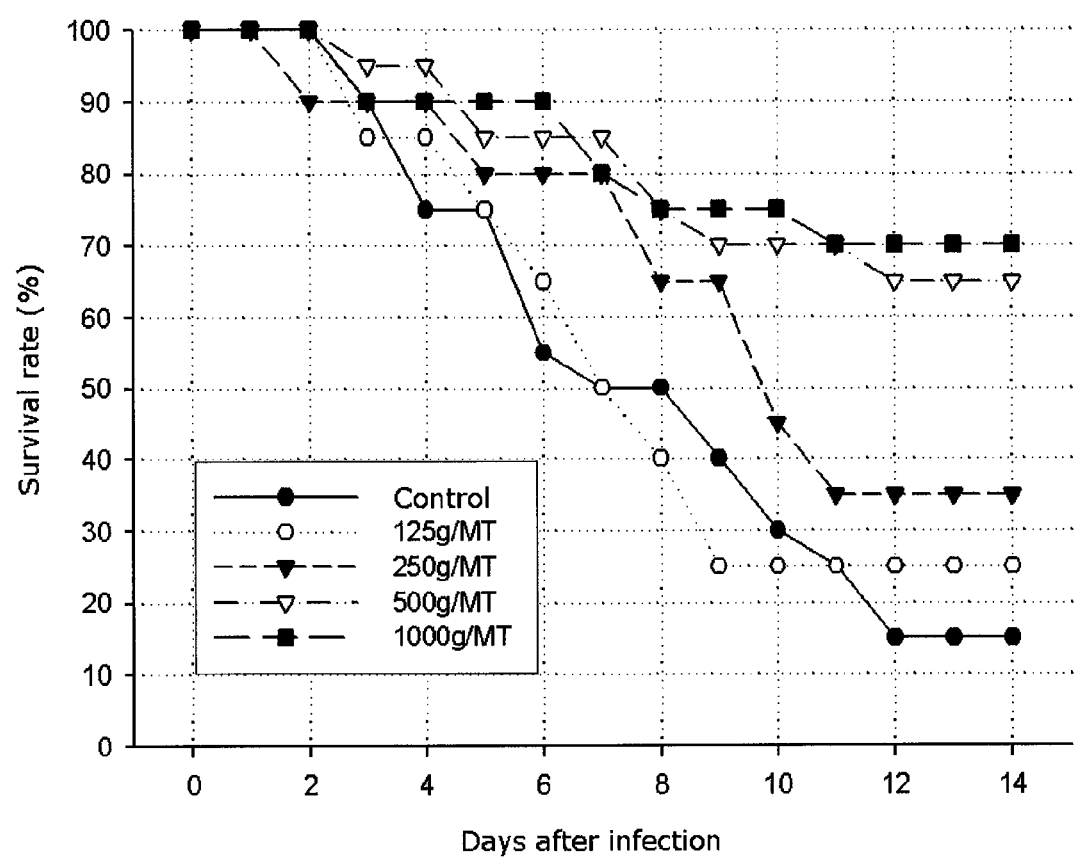

[Fig. 5]
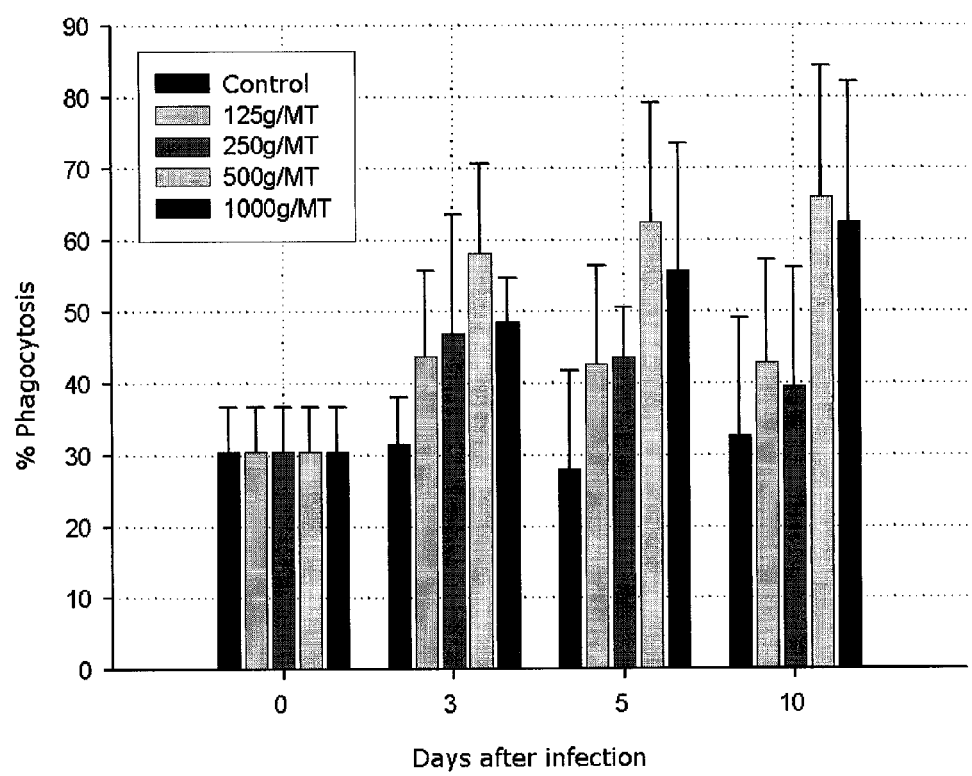

[Fig. 6]
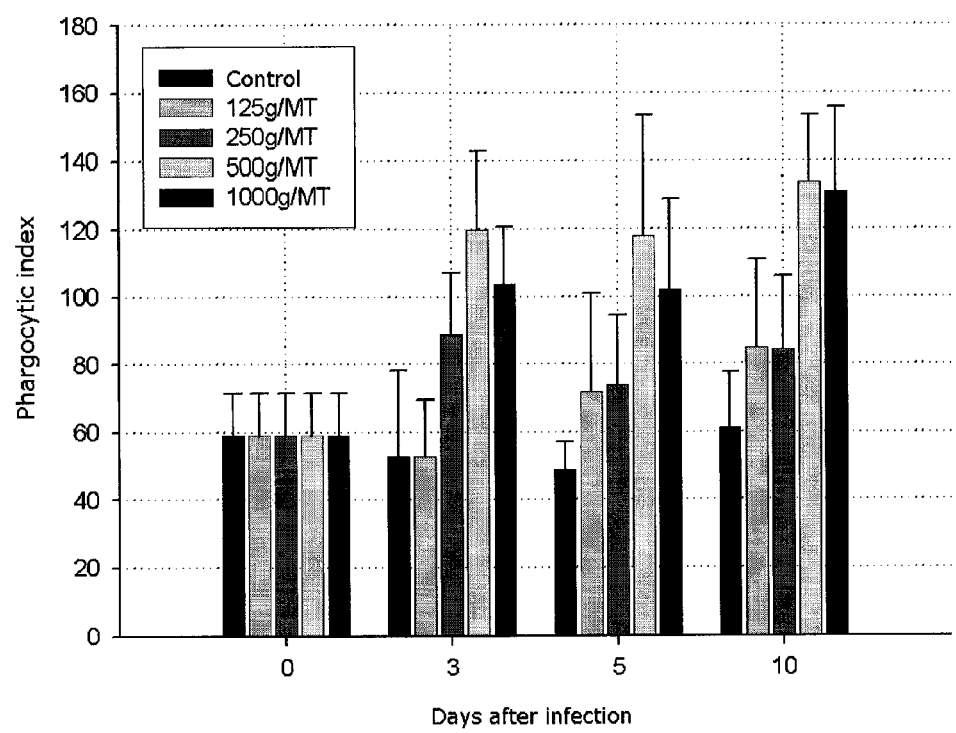

COMPOSITION AND METHOD FOR TREATING OR PREVENTING WHITE SPOT SYNDROME VIRUS

TECHNICAL FIELD

The present invention relates to a composition and method for treating or preventing white spot syndrome virus.

BACKGROUND ART

World shrimp industry has grown until the early 1990's without any threatening of severe diseases. Vibriosis was a major disease threatening the farming yield of shrimp in the late 1980s and the early 1990s. However, new deadly viruses like yellow head virus, white spot syndrome virus, Taura syndrome virus, etc. were introduced in the 1990s, which exerted a severe bad effect on shrimp farming yield.

Particularly, white spot syndrome virus of shrimp is broadly happening from Asia, including Korea and Japan, to Central and South America, and then its economic damage is very severe. White spot syndrome virus is a double-stranded DNA virus of which host is various kinds of crustaceans, and belongs to genus *Whispovirus* and family Nimaviridae (van Hulten M. C. W et al., J. Gen. Virol., 81, pp 307-316, 2000). Virion is relatively large (80-120 nm×250-380 nm) and has three pellicles, and its shape is rod or oval. After an arthropod like shrimp, crayfish, crab, etc. is infected with white spot syndrome virus, white spot happens on integument of shrimp like gills, mesothelium, carapace, appendage, cuticle, etc. and infected arthropod shows lethargy, reduced movement, and sudden reduction in food consumption. 3~5 days after the infection, infected arthropod falls dead (J. M. Vlak et al., XII International Congress of Virology, Paris, 2002).

According to scientists discovering the virus and areas, the white spot syndrome virus is also called as WSSV (white spot syndrome virus), WSV (white spot virus), WSBV (white spot baculovirus), CBV (Chinese baculo-like virus, HHNBV (hypodermal and hematopoietic necrosis baculovirus), PV-PJ (rod shaped virus of *Penaeus japonicus*), PRDV (penaeid rod-shaped dovavirus), PAV (penaeid acute viremia), SEMBV (systemic ectodermal and mesodermal baculo-like virus) and so on. However, those viruses are identified as the same virus.

There are many studies and developments to decrease a damage of white spot syndrome virus, and most studies and developments are focused on immuno-stimulation of arthropod. Lipopolysaccharide, glucan, fucoidan and so on are conventionally used, but their effects are not enough to substantially reduce the damage of the virus. In addition, chitosan, saponin, lactoferrin, dextran, inulin, etc. are reported to have some effect (Newman S. G., Fifth Ecuadorian Aquaculture Conference, October pp 28-30, 1999).

Use of plant extract as anti-virus medicine has been tried from a long time ago, and recently effects of some plant extracts are scientifically investigated. Some plant extracts are reported to have anti-virus effect on white spot syndrome virus of shrimp. For example, *Clinacanthus nutans* (Direkbusarakom S., et al., Fish Pathology, 33(4), pp 410-404, 1998) and some conventional plants (Direkbusarakom S., et al., Fish Pathology, 31(4), pp 209-213, 1996) of Thailand, and *Phyllanthus* spp. plants (Direkbusarakom S., et al., Diseases in Asian Aquaculture II. Manila, pp 81-88, 1995) are studied. In South Korea, licorice root, *Cnidium officinale*, peanut, buck wheat, *Codium fragile* and layer are also reported to have some suppressing effect on white spot syndrome virus. However, there is a need for a composition having better treating or preventing effect on white spot syndrome virus.

DISCLOSURE

Technical Problem

Accordingly, the object of the present invention is to provide a composition and method being useful in treating or preventing white spot syndrome virus.

Technical Solution

To achieve the object, the present invention provides a composition for treating or preventing white spot syndrome virus of arthropod like shrimp, crayfish, crab, etc., comprising *Artemisia japonica* extract as effective agent. More preferably, the present invention provides the composition for treating or preventing white spot syndrome virus of arthropod, comprising *Artemisia japonica* extract and *Saururus chinensis* extract as effective agents.

The present invention also provides a method for treating or preventing white spot syndrome virus of arthropod like shrimp, crayfish, crab, etc., using *Artemisia japonica* extract and more preferably, using both *Artemisia japonica* extract and *Saururus chinensis* extract.

More preferably, the present invention provides the composition and the method wherein the mixing weight ratio of *Artemisia japonica* extract and *Saururus chinensis* extract is from 7:3 to 3:7.

Preferably, the present invention provides the composition and the method wherein *Artemisia japonica* extract and *Saururus chinensis* extract are coated with a polymer and more preferably, the composition and the method wherein *Artemisia japonica* extract and *Saururus chinensis* extract are made into granules and then coated with a polymer.

More preferably, the present invention provides the composition and the method wherein *Artemisia japonica* extract and *Saururus chinensis* extract are made into granules, and then firstly coated with a hydrophilic polymer and secondly coated with a non-hydrophilic polymer.

More preferably, the present invention provides the method for treating or preventing white spot syndrome virus, wherein the total supplying amount of *Artemisia japonica* extract and *Saururus chinensis* extract is 300 to 700 g per one ton of general feed.

Hereinafter, the composition and method for treating or preventing white spot syndrome virus according to the present invention will be described in more detail.

The present invention is based on the surprising fact that *Artemisia japonica* extract, preferably, the mixture of *Artemisia japonica* extract and *Saururus chinensis* extract is useful in treating or preventing white spot syndrome virus of an arthropod like shrimp, crayfish, crab, etc. From this surprising fact, the present invention provides a composition for treating or preventing white spot syndrome virus, comprising *Artemisia japonica* extract, preferably, both *Artemisia japonica* extract and *Saururus chinensis* extract as effective agent. The present invention also provides a method for treating or preventing white spot syndrome virus, using *Artemisia japonica* extract, preferably, *Artemisia japonica* extract and *Saururus chinensis* extract together.

The present invention is also based on the fact that *Artemisia japonica* extract is more useful than other plants belonging to *Artemisia* species in treating or preventing white spot syndrome virus.

The present invention is also based on the surprising fact that the mixing of *Artemisia japonica* extract and *Saururus chinensis* extract synergically increases the effect of treating or preventing white spot syndrome virus. The mixture of *Artemisia japonica* extract and *Saururus chinensis* extract according to the present invention shows synergically increased effect than *Artemisia japonica* extract alone or *Saururus chinensis* extract alone. Preferably, the mixing weight ratio of *Artemisia japonica* extract and *Saururus chinensis* extract is 7:3 to 3:7 and more preferably, 6:4 to 4:6.

*Artemisia japonica* extract and/or *Saururus chinensis* extract of the present invention can be made according to extracting methods well known in the art. For example, the plant extracts are prepared as follows: about 1-15 times volume of solvent such as water, ethanol, methanol, propanol, butanol, acetone, ethylacetate or their mixture are added to *Artemisia japonica* and/or *Saururus chinensis*, and then plant extracts are prepared by cold water immersion method, heat extraction method, reflux-cooling extraction method, etc. Then, the plant extracts are filtered by filter paper having an appropriate size (for example, filter paper having 10 um of pore size), and the filtrate are concentrated in vacuo, distillation-concentrated under reduced pressure or concentrated by spray-drying at a proper temperature (for example, about 30-70° C.) to get a *Artemisia japonica* extract or *Saururus chinensis* extract.

It is preferable to make the plant extracts into granules before coating. The extracts are mixed with conventionally used diluents in the art (for example, maltodextrin, lactose, microcrystalline cellulose, sucrose, mannitol and starch) or general shrimp feed, and then prepared into granules according to well-known methods in the art like dry-granulation method, wet-granulation method, simple mixing method, etc. This granulation is preferable in aspects of mixing efficiency with general feed, easiness in handling and the following coating process.

Furthermore, it is preferable for the following processes to add about 0.1-5% (based on the total weight of granules) of lubricant (for example, silicone dioxide and magnesium stearate) into prepared granules.

The present invention also provides the surprising fact that it can epochally improve intake rate of shrimp to coat the *Artemisia japonica* extract and *Saururus chinensis* extract with a polymer. This improvement is thought to be achieved by the coated polymer's blocking the smell of *Artemisia japonica* extract and *Saururus chinensis* extract, but the present invention is not limited to this presumption.

As said above, preferably, *Artemisia japonica* extract and *Saururus chinensis* extract of the present invention are made into granules for easiness of coating process and then coated by a polymer. When considering several aspects, it is preferable to firstly coat the extract with a hydrophilic polymer and then secondly coat the firstly coated extract with a non-hydrophilic polymer. In case that the hydrophilic polymer only is used for coating, it is difficult to block smell of the plant extract because the hydrophilic polymer is easily dissolved in water. In case that the non-hydrophilic polymer only is used, a lot of non-hydrophilic polymer must be used to block the smell or taste of the extract, and this lots of amount is difficult to be dissolved in water, which may cause the reduction of efficacy. In addition, the first coating itself is expected to show the effect blocking bad smell, but the second coating using the non-hydrophilic polymer is expected to improve the stability of the extract as well as the blocking effect of bad smell.

The hydrophilic polymer of the present invention means a polymer that can be easily dissolved in water even if lots of polymer is used for coating. This hydrophilic polymer includes, but is not limited to, hydroxymethylcellulose, hydroxyethylcellulose, hydroxyethylmethylcellulose, hydroxypropylmethylcellulose, hydroxypropylethylcellulose, carboxymethylcellulose, hydroxypropylcellulose, cellulose derivatives, sodium alginate, alginic acid, soybean protein, wheat protein, carrageenan, tragacanth gum, agar, arabia gum, guar gum, xanthan gum, gums, pectin, polyvinylalcohol, polymethylmethacrylate derivatives, polyvinylpyrrolidone, polyalkeneoxide, polyalkeneoxide derivatives, polyalkeneglycol, polyethylene-polypropylene polymer, polyoxyethylene-polyoxypropylene polymer, zein, diethylaminoacetate, aminoalkylmethacrylate copolymer, cyclodextrin, chitin, chitosan and gelatin. Hydroxymethylcellulose, hydroxyethylcellulose, hydroxyethylmethylcellulose, hydroxypropylmethylcellulose, hydroxypropylethylcellulose, carboxymethylcellulose, hydroxypropylcellulose, cellulose derivatives, sodium alginate, alginic acid, polyvinylalcohol and polyvinylpyrrolidone are more preferable.

The non-hydrophilic polymer of the present invention means a polymer that is difficult to be dissolved or is very slowly dissolved in water so that the polymer can prevent the extract from being dissolved into water in a short time. This non-hydrophilic polymer includes, but is not limited to, methylcellulose, ethylcellulose, shellac, polyvinylacetate, poly-L-lysine, hydroxypropylmethylcellulose phthalate, high-viscous cellulose derivatives, hydroxypropylmethylcellulose acetate succinate, cellulose acetate phthalate, corn protein extract, corn protein extract derivatives, soybean protein, wheat protein, chitin, chitic acid, agar, pectin, gums and polymethylmethacrylate derivatives. Ethylcellulose, methylcellulose and shellac are more preferable.

Preferably, the amount of the first coating using the hydrophilic polymer is 1-30 wt % based on the total weight of the extract granules, and more preferably, 4-15 wt %. Preferably, the amount of the second coating using the non-hydrophilic polymer is 1-10 wt % based on the total weight of the first coated granules, and more preferably 2-8 wt %.

In case of the first coating, water can be used for making a coating solution. In case of the second coating, ethanol, methanol, isopropanol, acetonitrile, acetone, ether, hexane, chloroform, 1,4-dioxane, dimethylsulfoxide, tetrahydrofuran, ethylacetate, methylacetate or their mixture can be used for making a coating solution.

The coating can be performed with conventional machines well known in the art, like a fluidized bed granulator, a spray drier, C/F granulator, etc. The scope of the present invention is not limited to these machines.

In the method for treating or preventing white spot syndrome virus, particularly of shrimp, the total supplying amount of *Artemisia japonica* extract and *Saururus chinensis* extract is preferably 300 to 700 g and more preferably 400 to 600 g per one ton of general feed on the basis of 1% supply (per one day) of the body weight of one shrimp. Supplying over 700 g is not economical because the effect does not improve over 700 g. In case of supplying less than 300 g, the medicinal effect of the extract may not be enough to treat or prevent white spot syndrome virus of shrimp.

BRIEF DESCRIPTION OF THE DRAWINGS

FIG. 1 shows efficacy evaluation results of *Artemisia japonica* extract, *Saururus chinensis* extract, *Artemisia capillaris* extract, *Artemisia gmelini* extract and *Houttuynia cordata* extract on white spot syndrome virus.

FIG. 2 shows efficacy evaluation results according the mixing ratio of *Artemisia japonica* extract and *Saururus chinensis* extract on white spot syndrome virus.

FIGS. 3 and 4 show efficacy evaluation results on white spot syndrome virus of shrimp according to supplying amounts of the coated *Artemisia japonica* extract and the coated *Saururus chinensis* extract per one ton of general feed.

FIGS. 5 and 6 are evaluation results showing a pharmacological mechanism of anti-white spot syndrome virus effect of the coated *Artemisia japonica* extract and the coated *Saururus chinensis* extract.

MODES FOR CARRYING OUT THE INVENTION

Hereinafter, the present invention is described in considerable detail to help those skilled in the art understand the present invention. However, the following examples are offered by way of illustration and are not intended to limit the scope of the invention. It is apparent that various changes may be made without departing from the spirit and scope of the invention or sacrificing all of its material advantages.

Example 1

Preparation of Extracts 5 kg of dried *Artemisia japonica*, *Saururus chinensis*, *Artemisia capillaris*, *Artemisia gmelini* and *Houttuynia cordata*, respectively, were immersion-extracted at room temperature with 50 liter of water, ethanol and their 1:1 mixture. The immersion-extraction was once performed for 3 days, and then re-performed for 2 days with no delay. Extracts were filtered by 10 um of filter paper and the filtrate was concentrated in vacuo at 60° C. until the weight of the filtrate decreased to 5% of the initial weight. The concentrate was made into granules with about 2.5 times of lactose based of the weight of the concentrate and about 2% of silicone dioxide based on the total weight.

When considering the yield of the concentrate, ethanol extraction was most efficient. Thus, extracts made with ethanol were used in the following all examples.

Example 2

Efficacy Evaluation of Each Extract on White Spot Syndrome Virus

Efficacy of extracts prepared in the example 1 on white spot syndrome virus was evaluated as follow:

Shrimp: *Palaemon paucidens* was used and their average body weight was 0.3 g. Shrimps were accustomed to experimental environments for one week before tests. During that accommodation period, general feed was supplied the shrimps.

Test samples: *Artemisia japonica* extract, *Saururus chinensis* extract, *Artemisia capillaris* extract, *Artemisia gmelini* extract and *Houttuynia cordata* extract of example 1 were used, respectively.

Test group: Control group was provided with general feed having no extracts. Five test groups were provided with *Artemisia japonica* extract, *Saururus chinensis* extract, *Artemisia capillaris* extract, *Artemisia gmelini* extract and *Houttuynia cordata* extract, respectively. 30 shrimps were included in each group.

Feeding of test samples: Test samples were supplied everyday for 7 days before infection of the virus to evaluate preventing and treating effect on white spot syndrome virus. In addition, test samples were supplied everyday until 7 days after the infection of the virus. Feeding was performed at a.m. 10 o'clock everyday.

Raising conditions of shrimp: Shrimps were raised in 10 liter of water bath. The temperature of the bath was kept at 20° C.

Infection of white spot syndrome virus: Shrimps were artificially infected with white spot syndrome virus and died finally. Three died shrimps were finely ground in 10 ml of distilled water. The ground solution was added to the water bath as 3500:1 of ratio to infect shrimps in water bath with white spot syndrome virus. After the infection, mortality rates of shrimps were evaluated.

Results were shown in FIG. 1. As shown in the FIG. 1, *Artemisia japonica* extract, *Saururus chinensis* extract and *Artemisia capillaries* extract increased the survival rate of shrimps in comparison with control, which means that those extracts are useful in treating or preventing white spot syndrome virus. In addition, *Artemisia japonica* extract was more effective than *Saururus chinensis* extract and *Artemisia capillaries* extract.

Example 3

Efficacy Evaluation of the Mixture of Extracts Mixture on White Spot Syndrome Virus Efficacy of a mixture of *Artemisia japonica* extract and *Saururus chinensis* extract on white spot syndrome virus was evaluated, and a proper mixing ratio of the mixture was investigated as follows:

Shrimp: *Palaemon paucidens* was used and their average body weight was 0.3 g. Shrimps were accustomed to experimental environments for one week before tests. During that accommodation period, general feed was supplied the shrimps.

Test samples: *Artemisia japonica* extract and *Saururus chinensis* extract prepared in the example 1 were used.

Test group: Control group was provided with general feed having no *Artemisia japonica* extract and *Saururus chinensis* extract. Five test groups were provided with mixtures of *Artemisia japonica* extract and *Saururus chinensis* extract having mixing ratios of 10:0, 6:4, 5:5, 4:6 and 0:10, respectively. 30 shrimps were included in each group.

Feeding of test samples: Test samples were supplied everyday for 7 days before infection of the virus to evaluate preventing and treating effect on white spot syndrome virus. In addition, test samples were supplied everyday until 7 days after the infection of the virus. Feeding was performed at a.m. 10 o'clock everyday.

Raising conditions of shrimp: Shrimps were raised in 10 liter of water bath. The temperature of the bath was kept at 20±1° C.

Infection of white spot syndrome virus: Shrimps were artificially infected with white spot syndrome virus and died finally. Three died shrimps were finely ground in 10 ml of distilled water. The ground solution was added to the water bath as 3500:1 of ratio to infect shrimps in water bath with white spot syndrome virus. After the infection, the mortality rates of shrimps were evaluated.

Results were shown in FIG. 2. As shown in the FIG. 2, *Artemisia japonica* extract, *Saururus chinensis* extract and their mixture increased the survival rate of shrimps in comparison with control. Mixture of *Artemisia japonica* extract and *Saururus chinensis* extract having almost equal mixing ratio, particularly 6:4 weight ratio mixture of *Artemisia japonica* extract and *Saururus chinensis* extract, showed superior survival rate than the other test samples.

However, when *Artemisia japonica* extract and *Saururus chinensis* extract were administered by simple mixing with general feed, lots of test samples were not eaten by shrimps and remained, which was thought to be caused by the unique smell of the extracts. Because of this problem, difficulty was expected in letting shrimps eat enough extracts and there was a need to improve a feed intake rate of shrimp.

Example 4

Coating of Extract

Extracts were coated with polymer like the below examples to block the unique smell of the extracts, that is, to increase shrimp's intake rate of *Artemisia japonica* extract and *Saururus chinensis* extract.

Example 4-1

① The First Coating 100 g of hydroxypropylmethylcellulose (HPMC2910) was dissolved into 1,000 ml of distilled water to make a coating solution. 1,000 g of 6:4 (weight) mixture of *Artemisia japonica* extract granule and *Saururus chinensis* extract granule, prepared in the example 1, were fluidized in a fluidized bed granulator (GX40, Freund, Japan) and coated by spraying the coating solution. The preparing conditions of the fluidized bed granulator were as follows:
Inlet air temperature: about 6° C.
Flow rate of inlet air: 0.3 l/minute
Flow rate of outlet air: 0.5 l/minute
Rotor rotation number: 220 rpm
Spraying speed: 10 ml/minute ② The Second Coating 49.5 g of ethylcellulose was dissolved in a mixture of 385 ml of acetone and 110 ml of ethanol to make a coating solution. The above coated granules were fluidized in the fluidized bed granulator and coated by spraying the second coating solution. The preparing conditions of the fluidized bed granulator were as follows:
Inlet air temperature: about 50° C.
Flow rate of inlet air: 0.3 l/minute
Flow rate of outlet air: 0.5 l/minute
Rotor rotation number: 230 rpm
Spraying speed: 12 ml/minute Example 4-2

① The First Coating 3 g of sodium alginate was dissolved in 1,000 ml of distilled water to make a coating solution. 1,000 g of 6:4 (weight) mixture of *Artemisia japonica* extract granule and *Saururus chinensis* extract granule, prepared in the example 1, and 97 g of lactose were fluidized in the fluidized bed granulator and coated by spraying the coating solution. The preparing conditions of the fluidized bed granulator were similar to those of the first coating of the example 4-1.

② The Second Coating 49.5 g of hydroxypropylmethylcellulose phthalate (HP-MCP) was dissolved in a mixture of 247.5 ml of acetone and 247.5 ml of ethanol to make a coating solution. The above coated granules were fluidized in the fluidized bed granulator and coated by spraying the second coating solution. The preparing conditions of the fluidized bed granulator were similar to those of the second coating of the example 4-1.

Example 4-3

① The First Coating 100 g of hydroxypropylmethylcellulose (HPMC2910) was dissolved in 1,000 ml of distilled water to make a coating solution. 1,000 g of 6:4 (weight) mixture of *Artemisia japonica* extract granule and *Saururus chinensis* extract granule, prepared in the example 1, was fluidized in the fluidized bed granulator and coated by spraying the coating solution. The preparing conditions of the fluidized bed granulator were similar to those of the first coating of the example 4-1.

② The Second Coating 49.5 g of shellac was dissolved in 495 ml of ethanol to make a coating solution. The above coated granules were fluidized in the fluidized bed granulator and coated by spraying the second coating solution. The preparing conditions of the fluidized bed granulator were similar to those of the second coating of the example 4-1.

Example 5

Intake Rate Evaluation of Coated Extract Granules

Test feeds for shrimp were made with coated extract granules prepared in the above examples 4-1 to 4-3. Intake rates according to the kind of coating polymer were evaluated as follows:
Shrimp: *Palaemon paucidens* was used and their average body weight was 0.3 g. Shrimps were accustomed to experimental environments for one week before tests. During that accommodation period, general feed was supplied the shrimps.
Test group: Control group was provided with feed having 6:4 (weight) mixture of uncoated *Artemisia japonica* extract granules and uncoated *Saururus chinensis* extract granules, prepared in example 1. 30 shrimps were included in each group.
Feeding of test samples: Test samples were supplied from the $0^{th}$ day to the $5^{th}$ day, wherein the $0^{th}$ day was the day after one week of the above accommodation period ended. 2 g of feed was supplied once a day, and feeding was performed at a.m. 10 o'clock everyday.
Raising conditions of shrimp: Shrimps were raised in 10 liter of water bath. The temperature of the bath was kept at 20±1° C.
Evaluation items: From the $0^{th}$ day to the $5^{th}$ day of feeding test samples, the remaining amount of feed supplied in the previous day was recorded everyday at the same time of feeding as 5 points (from 1 to 5) according to the remaining amount in water bath. After the evaluation of the remaining amount, water bath were cleaned and shrimps were supplied new feeds. After dividing the bottom of the bath into 6 parts (3 partitions in the width and 2 partitions in the length), points were granted as follows: grade 0 (−)—all 6 parts have no remaining feed; grade 1 (+)—one part among 6 parts has remaining feed; grade 2 (++)—two parts have remaining feed; grade 3 (+++)—three parts have remaining feed; grade 4 (++++)—four parts have remaining feed; and grade 5 (+++++)—five or all parts have remaining feed. Results were shown in table 1 below.

TABLE 1

|  | 1st day | 2nd day | 3rd day | 4th day | 5th day |
| --- | --- | --- | --- | --- | --- |
| Control | ++++ | +++ | ++++ | ++++ | +++ |
| Example 4-1 | ++ | + | + | + | + |
| Example 4-2 | +++ | ++ | ++ | +++ | ++ |
| Example 4-3 | ++ | ++ | +++ | ++ | ++ |

As shown in the table 1, groups provided with examples 4-1 to 4-3 having coated samples showed higher intake rate than control group provided with uncoated extracts. Particularly, example 4-1 showed the highest intake rate of feed.

Example 6

Evaluation of Treating and Preventing Effect against White Spot Syndrome Virus According to the Supply Amount As said in the followings, the treating and preventing effect against white spot syndrome virus was evaluated according to the supply amount of coated extracts.

Shrimp: Kuruma shrimp (*Maruspenaeus japonicus*) was used and the average body weight of the shrimps was 10.5-18.9 g. 17-20 shrimps were included in each group. Shrimps were accustomed to experimental environments for two weeks before test. During the accommodation period, general feed was supplied.

Test sample: The coated extract granules prepared in the example 4-1 were used.

Test feed: Gold Prawn (Higashimaru, Kagoshima, Japan) was used as test feed. 0 g, 125 g, 250 g, 500 g or 1000 g of the test sample was added per one ton of the test feed. The supply amount of test feed was 1% (per one day) of the body weight of one shrimp.

Feeding of test feed: Test feed was supplied everyday from 7 days before infection of the virus to 14 days after infection of the virus. Feeding of test feed was performed p.m. 6 o'clock everyday.

Raising conditions of shrimp: Shrimps were raised in 60 liter of water bath. The temperature of the bath was kept at 21±1° C.

Infection of white spot syndrome virus: Shrimps were artificially infected with white spot syndrome virus and died finally. Three died shrimps were finely ground in 10 ml of sterilized sea water. The ground solution was diluted with sterilized sea water as 8000:1 of ratio to make a virus infection solution. Infection of virus was performed by soaking shrimps of each group in the virus infection solution for two hours and then again transferring the shrimps into the 60 liter of water bath. After the infection, mortality rate was evaluated for 10 days.

Evaluation item: After the infection of virus, the mortality rate of each group and conventional symptoms of white spot syndrome virus were evaluated.

Example 6 was twice performed and results were shown in FIGS. 3 and 4, respectively. As shown in FIGS. 3 and 4, groups administered with test samples showed higher survival rate than control group. Especially, groups administered with 500 g and 1,000 g of test samples showed much higher survival rate than control group. These results show that adding more than 500 g of coated extracts granules per one ton of general feed can efficiently treat or prevent white spot syndrome virus of shrimp in case of being administered by an supply amount of 1% of the body weight per one shrimp everyday.

Example 7

Pharmacological Mechanism of the Extracts on White Spot Syndrome Virus

Hematocyte cells were collected from shrimps of each test group used in the example 6 to investigate the phagocytic activity of the hematocyte cells. Collection of hematocyte cells was performed by directly pulling out hemolymph from the heart of shrimp with a syringe filled with KC-199 medium [11 g NaCl; 0.4 g KCl; 3 g $MgSO_4.7H_2O$; 3 g $MgCl_2.6H_2O$; 0.9 g $CaCl_2.2H_2O$; 0.05 g $NaH_2PO_4.2H_2O$; and 0.15 g L-glutamine in 1 liter, to which 50 g of L-cysteine (anti-coagulant) was added and medium's pH was adjusted to 7.6 with 6N NaOH]. Collected hematocytes were washed by centrifugation (2500 rpm, 10 minutes, 4° C.) in K-199 medium [L-cysteine was removed in comparison with KC-199 and medium's pH was adjusted to 7.6 with $NaHCO_3$]. Washed hematocytes ($1 \times 10^5$ cells/ml) were transferred to Petri dish including K-199 medium and fluorescence-labeled latex bead ($1 \times 10^8$ beads/ml) and mixed well. Cover glass for microscope was laid on the mixture of hematocytes and beads, and incubated for 30 minutes at 25° C. and fixed with glutaraldehyde. Cover glass to which hematocytes were attached was turned upside down and laid on fluorescence microscope for 400× observation. The number of phagocytized beads and phagocytizing cells were counted among 300 of hematocytes in the cover glass. Under the same conditions, the above experiment was repeated three times per one shrimp. Phagocytic index (PI) and phagocytosis percent (% P) were calculated according to the blow math equation 1 and 2. The same experiments were repeated twice and the results were shown in FIGS. 5 and 6, respectively.

$$PI = (\text{the number of cells phagocytizing bead/the total number of observed cells}) \times (\text{the number of phagocytized beads/the total number of observed cells}) \times 100 \qquad \text{[Math Equation 1]}$$

$$\% P = (\text{the number of cells phagocytizing bead/the total number of observed cells}) \times 100 \qquad \text{[Math equation 2]}$$

As shown in FIGS. 5 and 6, test groups provided with test samples showed higher phagocytosis activity of hematocytes than control group. Particularly, test groups provided with 500 g and 1,000 g of test samples showed much higher phagocytosis activity than control group. These results show that the preventing effect of plant extracts of the present invention is very efficacious, and this preventing effect is thought to be linked with the increase of resistance to the disease, which is thought to causes the increase of hemotocyte's phagocytic activity. From these results, the effect of plant extracts of the present invention on white spot syndrome virus of shrimp is guessed to be caused by the activation of hematocytes and direct phagocytosis against the virus.

INDUSTRIAL APPLICABILITY

As shown above, the present invention provides a composition for treating or preventing white spot syndrome virus, comprising *Artemisia japonica* extract, or more preferably, *Artemisia japonica* extract and *Saururus chinensis* extract as effective agent. The present invention also provides a method for treating or preventing white spot syndrome virus, using the composition.

What is claimed is:

1. A method for treating white spot syndrome in a shrimp, crayfish and/or crab which comprises administering to the shrimp, crayfish and/or crab a therapeutically effective amount of *Artemisia japonica* extract.

2. The method of claim 1, further comprising administering a therapeutically effective amount of *Saururus chinensis* extract.

3. The method of claim 2, wherein the mixing weight ratio of *Artemisia japonica* extract and *Saururus chinensis* extract is from 7:3 to 3:7.

4. The method of claim 2, wherein the *Artemisia japonica* extract and *Saururus chinensis* extract are coated with a polymer.

5. The method of claim 4, wherein the *Artemisia japonica* extract and *Saururus chinensis* extract are made into granules before being coated with a polymer.

6. The method of claim 3, wherein the *Artemisia japonica* extract and *Saururus chinensis* extract are firstly coated with a hydrophilic polymer and secondly coated with a non-hydrophilic polymer.

7. The method of claim 3, wherein the total supplying *Artemisia japonica* extract and *Saururus chinensis* extract are administered with general feed as a ratio of 300 to 700 g per one ton of general feed.

* * * * *